(12) United States Patent
Mammone et al.

(10) Patent No.: US 11,666,285 B2
(45) Date of Patent: Jun. 6, 2023

(54) METHOD FOR DETECTING A CONVERSION FROM MILD COGNITIVE IMPAIRMENT TO ALZHEIMER DISEASE

(71) Applicant: IRCCS CENTRO NEUROLESI "BONINO—PULEJO", Messina (IT)

(72) Inventors: Nadia Mammone, Reggio Calabria (IT); Francesco Carlo Morabito, Villa San Giovanni (IT); Placido Bramanti, Messina (IT); Alessia Bramanti, Messina (IT); Maurizio Campolo, Reggio Calabria (IT); Cosimo Ieracitano, Reggio Calabria (IT); Lilla Bonanno, Messina (IT)

(73) Assignee: IRCCS CENTRO NEUROLESI "BONINO-PULEJO", Messina (IT)

( * ) Notice: Subject to any disclaimer, the term of this patent is extended or adjusted under 35 U.S.C. 154(b) by 362 days.

(21) Appl. No.: 16/965,714

(22) PCT Filed: Jan. 30, 2019

(86) PCT No.: PCT/IB2019/050742
§ 371 (c)(1),
(2) Date: Jul. 29, 2020

(87) PCT Pub. No.: WO2019/150274
PCT Pub. Date: Aug. 8, 2019

(65) Prior Publication Data
US 2021/0030369 A1    Feb. 4, 2021

(30) Foreign Application Priority Data

Jan. 30, 2018  (IT) .......................... 102018000002183

(51) Int. Cl.
*A61B 5/00*       (2006.01)
*G16H 50/20*      (2018.01)
(Continued)

(52) U.S. Cl.
CPC ............ *A61B 5/7264* (2013.01); *A61B 5/369* (2021.01); *A61B 5/4088* (2013.01); *G06F 18/22* (2023.01);
(Continued)

(58) Field of Classification Search
CPC .................................................... A61B 5/4088
See application file for complete search history.

(56) References Cited

U.S. PATENT DOCUMENTS

2009/0024050 A1*  1/2009  Jung .................... A61B 5/4064
                                                       600/544
2013/0178731 A1*  7/2013  Bosl .................... A61B 5/7267
                                                       600/300
(Continued)

OTHER PUBLICATIONS

International Search Report of the International Searching Authority, dated Jul. 6, 2019 for corresponding PCT patent application No. PCT/IB2019/050742.
(Continued)

*Primary Examiner* — Devin B Henson
*Assistant Examiner* — Evelyn Grace Park
(74) *Attorney, Agent, or Firm* — Amster, Rothstein & Ebenstein LLP (57) ABSTRACT

A data processing method for detecting the conversion from mild cognitive impairment (MCI) to Alzheimer disease (AD), allowing objectively quantifying the effects that this has on the patient's electroencephalogram (EEG). The method of the invention provides an objective criterion for monitoring the brain health status of MCI subjects, which goes alongside the other criteria of neurological, psychological, clinical and cognitive assessment normally provided by the evaluation protocols of these patients.

11 Claims, 4 Drawing Sheets

(51) Int. Cl.
   A61B 5/369    (2021.01)
   G06F 18/22    (2023.01)
   G06F 18/231   (2023.01)
(52) U.S. Cl.
   CPC .......... *G06F 18/231* (2023.01); *G16H 50/20* (2018.01); *G06F 2218/18* (2023.01)

(56) References Cited

U.S. PATENT DOCUMENTS

| | | | | |
|---|---|---|---|---|
| 2020/0261013 | A1* | 8/2020 | Ben-Oren | G16H 20/70 |
| 2022/0079507 | A1* | 3/2022 | Epelbaum | A61B 5/7235 |
| 2022/0280065 | A1* | 9/2022 | Abeyratne | G06K 9/00536 |

OTHER PUBLICATIONS

Mammone N et al, "Hierarchical clustering of the electroencephalogram spectral coherence to study the changes in brain connectivity in Alzheimer's disease", 2016 IEEE Congress on Evolutionary Computation (CEC), IEEE, Jul. 24, 2016 (Jul. 24, 2016), p. 1241-1248.

Mammone N et al, "A Permutation Disalignment Index-Based Complex Network Approach to Evaluate Longitudinal Changes in Brain-Electrical Connectivity", ENTROPY, vol. 19, No. 10, Oct. 17, 2017 (Oct. 17, 2017), p. 548.

Sankari Z et al, "Wavelet Coherence Model for Diagnosis of Alzheimer Disease", Oct. 2012 (Oct. 2012), vol. 43, No. 4, p. 268-278.

Ieracitano C et al, "Wavelet coherence-based clustering of EEG signals to estimate the brain connectivity in absence epileptic patients", 2017 International Joint Conference on Neural Networks (IJCNN), IEEE, May 14, 2017 (May 14, 2017), p. 1297-1304.

Mammone N et al, "Permutation Jaccard Distance-Based Hierarchical Clustering to Estimate EEG Network Density Modifications in MCI Subjects", IEEE Transactions on Neural Networks and Learning Systems, vol. 29, No. 10, Oct. 2018 (Oct. 2018), p. 5122-5135.

\* cited by examiner

METHOD FOR DETECTING A CONVERSION FROM MILD COGNITIVE IMPAIRMENT TO ALZHEIMER DISEASE

CROSS REFERENCE TO RELATED APPLICATIONS

This application is a national phase of PCT application No. PCT/IB2019/050742, filed Jan. 30, 2019, which claims priority to IT patent application No. 102018000002183, filed Jan. 30, 2018, all of which are incorporated herein by reference thereto.

FIELD OF THE INVENTION

The present invention relates to a method for detecting the conversion from mild cognitive impairment (MCI=Mild Cognitive Impairment) to Alzheimer disease (AD=Alzheimer's Disease).

PRIOR ART

Today 47 million people are suffering from dementia all over the world. It is estimated that this number will grow to 131 million by the year 2050, as a result of the increase in the average age of the population. Alzheimer's Disease (AD) accounts for about 60% of dementia cases (World Alzheimer Report 2016) and is usually diagnosed after age 65. AD patients survive on average only 4 to 8 years after diagnosis, as this condition is still incurable.

AD is a neurodegenerative disease characterized by a subtle onset, which is estimated to begin decades before cognitive and memory problems become visible, and by gradual progression. AD upsets the metabolic processes that keep healthy neurons and causes nerve cells to stop functioning, lose interconnections with other neurons, and eventually die. The death of nerve cells causes memory deficits, personality changes, and problems in the performance of daily activities.

The group of experts from the National Institute on Aging and the Alzheimer Association (NIA/AA) has postulated that what is commonly considered "Alzheimer's disease" should rather be considered the stage of a more complex and long process of degeneration.

The experts of the NIA/AA have hypothesized three phases of progression of the AD:
1) Preclinical-AD: when the disease has already triggered the degeneration of the brain, but the clinical symptoms are not yet visible;
2) Mild Cognitive Impairment (MCI) caused by AD (MCI-AD or prodromal-AD): an intermediate phase in which symptoms related to the ability to think can start to be evident, but do not affect the daily life of the subject;
3) Dementia caused by AD (Dementia-AD): in the last phase of the evolution of the disease, disorders of memory, thought and behavior undermine a person's ability to live and act independently.

In fact, not all MCI subjects will develop dementia, since not all MCI subjects are inherently affected by AD. Only 10-15% of MCI patients "convert to AD" every year. Commonly there are two different types of AD: amnestic MCI (aMCI) and non-amnestic MCI. The first one refers to patients with memory deficits and the second one refers to patients with cognitive deficits but not memory deficits. aMCI subjects are more likely to develop AD.

Longitudinal studies (follow-up) on MCI patients are of fundamental importance to diagnose as soon as possible a possible progression of the MCI condition in AD, in order to be able to promptly take the treatment.

To this end, it is necessary to have tools for the quantitative assessment of the evolution of the state of health of the brain, in order to detect any progression towards dementia. The subjective clinical evaluation of the doctor must go alongside an instrument that quantifies the effects of the progression of the disease, so that the doctor can base his overall evaluation on different criteria, both subjective and objective.

Unfortunately, in the literature there are only a few longitudinal studies on MCI patients, with consequent lack of diagnostic tools to allow the neurologist to objectively monitor the progression of the disease.

SUMMARY OF THE INVENTION

A purpose of the present invention is to provide a method of objective assessment of the progression of MCI to AD, quantifying the effects it has on the patient's electroencephalogram (EEG).

The present invention achieves the above purpose by providing a method for detecting the conversion from mild cognitive impairment (MCI) to Alzheimer disease (AD), the method comprising the following stages:
a) providing as input data a plurality of first signals EEG $(1, \ldots, n)$ recorded at a first time $T_0$ and defining a first tracing EEG-$T_0$ of a patient with mild cognitive impairment, and a plurality of second signals EEG $(1, \ldots, n)$ recorded at a second time $T_1$ and defining a second tracing EEG-$T_1$ of the same patient, each first signal and each second signal corresponding to a respective electrode V (with V=1, ..., n), the first tracing EEG-$T_0$ and the second tracing EEG-$T_1$ being divided into epochs w of equal duration;
b) for each epoch w of the first tracing EEG-$T_0$ extracting at least two first sub-tracings $EEG_{sb}^{T0}$ corresponding to respective frequency sub-bands (sb=delta, theta, alpha, beta), and for each epoch w of the second tracing EEG-$T_1$ extracting at least two second sub-tracings $EEG_{sb}^{T1}$ corresponding to respective frequency sub-bands (sb=delta, theta, alpha, beta);
c) for each epoch w and for each of the first sub-tracings $EEG_{sb}^{T0}$ and second sub-tracings $EEG_{sb}^{T1}$, for each possible pair of signals x and y (with x=1, ..., n; y=1, ..., n and x≠y) calculating the Permutation Jaccard Distance $PJD_{x,y}$ (sb) between signal $EEG_{sb}(x)$ and signal $EEG_{sb}(y)$ at both time $T_0$ and time $T_1$;
d) for each first sub-tracing $EEG_{sb}^{T0}$ and each second sub-tracing $EEG_{sb}^{T1}$, performing a hierarchical clustering to divide into clusters the signals (and thus the respective electrodes) of the respective sub-tracing according to their mutual Permutation Jaccard Distances;
e) estimating the network density, when a fusion level FL varies, from the clusters obtained by the hierarchical Clustering (HC), defining two curves $ND^{T0}(sb)$ and $ND^{T1}(sb)$ for each frequency sub-band (sb=delta, theta, alpha, beta);
f) calculating the percentage variation $\Delta ND(sb)$ % of the area subtended by the two curves $ND^{T1}(sb)$ and $ND^{T0}(sb)$ for each frequency sub-band with the formula $\Delta ND(sb)\% = (ND^{T1}(sb) - ND^{T0}(sb))*100/ND^{T0}(sb)$;
g) verifying that said percentage variation $\Delta ND(sb)$ % is negative for each frequency sub-band in the transition from $T_0$ to $T_1$ to confirm the conversion from mild cognitive impairment (MCI) to Alzheimer disease (AD).

Advantageously, the method of the invention is based on the advanced processing of EEG signals since electroencephalography is a non-invasive neurophysiological evaluation technique, very well tolerated by patients, rapid, cost-effective and widespread on a large scale. The EEG is therefore the optimal candidate for the development of a system of early diagnosis of AD. The clinics in which the MCI and AD subjects are taken care of are normally equipped with EEG acquisition systems since the reporting of EEG tracing is part of the most widespread evaluation protocols of this category of patients.

The method of the invention is based on an innovative measure of synchronization of the EEG signals, called Permutation Jaccard Distance (PJD) and on its use as a measure of coupling between the electrodes. The electrodes are considered "nodes" of a complex network and the coupling between the nodes is estimated through the PJD. The network thus obtained is passed into input to the hierarchical clustering so that the electrodes are divided into clusters, according to the degree of coupling between them. The density of connectivity or network density (ND) between the electrodes, then between the corresponding brain areas, is estimated accordingly. Where the patient has progressed from MCI to AD, there is a significant increase in overall PJD and a significant decrease in ND because, due to cell death, phenomena of disconnection between cortical areas are triggered. However, this decrease is not observed in stable patients.

The proposed system thus provides an objective criterion for monitoring the brain health status of MCI subjects, which goes alongside the other criteria of neurological, psychological, clinical and cognitive assessment normally provided by the evaluation protocols of these patients.

Further features and advantages of the invention will appear more clearly from the detailed description of some exemplary but not exclusive embodiments thereof.

The dependent claims describe particular embodiments of the invention.

BRIEF DESCRIPTION OF THE FIGURES

In the description of the invention, reference is made to the accompanying drawings, which are given by way of non-limiting example, in which.

DETAILED DESCRIPTION OF EXEMPLARY EMBODIMENTS OF THE INVENTION

The method of the invention for detecting a conversion from mild cognitive impairment (MCI) to Alzheimer disease (AD), illustrated in the Figures, comprises the following stages:

a) providing as input data a plurality of first signals EEG (1, . . . , n), thus a first set of n signals, recorded at a first time $T_0$ and defining a first tracing EEG-$T_0$ of a patient with mild cognitive impairment, and a plurality of second signals EEG (1, . . . , n), thus a second set of n signals, recorded at a second time $T_1$ and defining a second tracing EEG-$T_1$ of the same patient, each first signal of said plurality of first signals and each second signal of said plurality of second signals corresponding to a respective electrode V (with V=1, . . . , n; thus, there are n electrodes), the first tracing EEG-$T_0$ and the second tracing EEG-$T_1$ being divided into epochs (or windows) w of equal duration;

b) for each epoch w of the first tracing EEG-$T_0$ extracting at least two first sub-tracings $EEG_{sb}^{T0}$ corresponding to respective frequency sub-bands (sb=delta, theta, alpha, beta), and for each epoch w of the second tracing EEG-$T_1$ extracting at least two second sub-tracings $EEG_{sb}^{T1}$ corresponding to respective frequency sub-bands (sb=delta, theta, alpha, beta);

c) for each epoch w and for each of the first sub-tracings $EEG_{sb}^{T0}$ and of second sub-tracings $EEG_{sb}^{T1}$, for each possible pair of signals x and y (with x=1, . . . , n; y=1, . . . , n and x≠y) calculating the Permutation Jaccard Distance $PJD_{X,Y}(sb)$ between signal $EEG_{sb}(x)$ and signal $EEG_{sb}(y)$ at both time $T_0$ and time $T_1$;

d) for each first sub-tracing $EEG_{sb}^{T0}$ and for each second sub-tracing $EEG_{sb}^{T1}$, performing a hierarchical clustering to divide into clusters the signals (and thus the respective electrodes) of the respective sub-tracing according to their mutual Permutation Jaccard Distances;

e) estimating the network density, when a fusion level FL varies, from the clusters obtained by the hierarchical Clustering, defining two network density curves $ND^{T0}(sb)$ and $ND^{T1}(sb)$ for each frequency sub-band (sb=delta, theta, alpha, beta);

f) calculating the percentage variation ΔND(sb) % of the area subtended by the two curves $ND^{T1}(sb)$ and $ND^{T0}(sb)$ for each frequency sub-band with the formula ΔND(sb) %= $(ND^{T1}(sb)-ND^{T0}(sb))*100/ND^{T0}(sb)$;

g) verifying that said percentage variation ΔND(sb) % is negative for each frequency sub-band in the transition from $T_0$ to $T_1$ to confirm the conversion from mild cognitive impairment (MCI) to Alzheimer disease (AD).

In other words, stage a) of the method provides, as input data, data of a plurality of first signals EEG (1, . . . , n) recorded at a first time $T_0$ and defining a first tracing EEG-$T_0$ of a patient with mild cognitive impairment, and data of a plurality of second signals EEG (1, . . . , n) recorded at a second time $T_1$ and defining a second tracing EEG-$T_1$ of the same patient, each first signal and each second signal corresponding to a respective electrode V (with V=1, . . . , n), and the first tracing EEG-$T_0$ and the second tracing EEG-$T_1$ being divided into epochs (w) of equal duration;

or stage a) includes dividing a first tracing EEG-$T_0$ of a patient with mild cognitive impairment, defined by a plurality of first signals EEG (1, . . . , n) recorded at a first time $T_0$, and a second tracing EEG-$T_1$ of the same patient, defined by a plurality of second signals EEG (1, . . . , n) recorded at a second time $T_1$, in epochs w of equal duration;

or, more simply, stage a) includes dividing a first tracing EEG-$T_0$, defined by a plurality of first signals EEG (1, . . . , n), and a second tracing EEG-$T_1$, defined by a plurality of second signals EEG (1, . . . , n), in epochs w of equal duration.

It should be noted that the whole method of the invention is based on an EEG tracing data processing. Carrying out the method of the invention never requires the presence of the human body. The whole method must be executed offline once the input data, i.e. the data of the two EEG tracings previously recorded at time $T_0$ (baseline) and at time $T_1$ (some months after $T_0$, for example 2 or 3 or 4 or 5 months after $T_0$) have been stored on a computer.

The data processing, provided for in the steps of the method of the invention, can be performed by any computer on which a software adapted to execute said steps is installed.

It is preferable that the EEG tracings, once memorized, are reviewed by an EEG expert in order to identify, preferably visually, and eliminate tracing segments contaminated by artifacts. The EEG tracings, thus cleaned up by the artifacts, will be subsequently processed according to the method of the invention.

In one embodiment of the invention, between stage c) and stage d) for each first sub-tracing $EEG_{sb}^{T0}$ and each second sub-tracing $EEG_{sb}^{T1}$ the following is provided calculating the respective average values $PJD^{T0}_{X,Y}(sb)$, $PJD^{T1}_{X,Y}(sb)$ on all the epochs w for each possible pair of signals $EEG_{sb}(x)$ and $EEG_{sb}(y)$, said average values $PJD^{T0}_{X,Y}(sb)$ and $PJD^{T1}_{X,Y}(sb)$ defining the dissimilarities $D_{X,Y}^{T0}(sb)$ and $D_{X,Y}^{T1}(sb)$ between the signal $EEG_{sb}(x)$ and the signal $EEG_{sb}(y)$ of each possible pair, at time $T_0$ and at time $T_1$, respectively;

building two networks $NET_{sb}(T_i)$, with i=0, 1, the node "x" of which represents the signal $EEG_{sb}(x)$ (thus the electrode "x") at time $T_i$, and the weight connecting the nodes "x" and "y" of the network $NET_{sb}(T_i)$ represents the dissimilarity between the pair of signals $EEG_{sb}(x)$ and $EEG_{sb}(y)$ at time $T_i$, thus creating two dissimilarity matrices $D^{T0}(sb)$ and $D^{T1}(sb)$, the (x, y)-th element of which is equal to $D_{X,Y}^{T0}(sb)=PJD_{X,Y}^{T0}(sb)$ and $D_{X,Y}^{T1}(sb)=PJD_{X,Y}^{T1}(sb)$, respectively.

In stage d) the hierarchical Clustering is performed, starting from the dissimilarity matrices $D^{T0}(sb)$ and $D^{T1}(sb)$, outputting two dendrograms showing the connection between the first signals $EEG_{sb}(1, \ldots n)$ at time $T_0$ and the connection between the second signals $EEG_{sb}(1, \ldots n)$ at time $T_1$, respectively, as a function of a fusion level FL, whereby for each dissimilarity matrix and for each fusion level FL, a set of clusters is determined.

Preferably, the hierarchical Clustering is performed by an agglomerative hierarchical Clustering algorithm, preferably a "complete linkage algorithm", also referred to as "furthest neighbour", which defines the distance or dissimilarity between two clusters by means of the maximum distance between a pair of signals, a signal belonging to a first cluster while the other signal of said pair belonging to the second cluster.

In stage e), the following is provided for each fusion level FL, calculating the number of active connections $AC_{FL}^{T0}(sb)$ and $AC_{FL}^{T1}(sb)$ respectively by summing the number of possible pairs of first signals $EEG_{sb}(1, \ldots n)$ at time $T_0$, and by summing the number of possible pairs of second signals $EEG_{sb}(1, \ldots n)$ at time $T_1$, present within each cluster of the respective set of clusters;

for each fusion level FL, estimating the network densities $ND_{FL}^{T0}(sb)$ and $ND_{FL}^{T1}(sb)$ by normalizing $AC_{FL}^{T1}(sb)$ and $AC_{FL}^{T1}(sb)$, respectively, with respect to the total number of possible connections equal to $[n*(n-1)/2]$, where n is the number of signals.

The network densities $ND_{FL}^{T0}(sb)$ and $ND_{FL}^{T1}(sb)$ are estimated for different fusion levels from 0 to 1, preferably but not necessarily with steps of 0.01.

In stage c), before calculating the Permutation Jaccard Distance $PJD_{X,Y}(sb)$ for each possible pair of signals $EEG_{sb}(x)$ and $EEG_{sb}(y)$, the following is provided:

c1) for each possible pair of signals $EEG_{sb}(x)$ and $EEG_{sb}(y)$ which is mappable in a m-dimensional space, where m is the embedding dimension, each signal $EEG_{sb}(x)$, $EEG_{sb}(y)$ having N time samples (t, t+1, . . . , t+N−1) in said epoch w, detecting a plurality of symbols (patterns or motifs) $\pi_i, \pi_j$, with i, j=1, . . . , m!, occurring in said epoch w for each sample (t, t+1, . . . , t+N−1);

c2) for each sample (t, t+1, . . . , t+N−1), detecting the number of occurrences $\eta_X(\pi_i)$ of each motif $\pi_i$ along the signal $EEG_{sb}(x)$, the number of occurrences $\eta_Y(\pi_j)$ of each motif $\pi_j$ along the signal $EEG_{sb}(y)$, and the number of joint occurrences $\eta_{X,Y}(\pi_i,\pi_j)$ of the two motifs $\pi_i$, $\pi_j$ along said signal $EEG_{sb}(x)$ and said signal $EEG_{sb}(y)$;

c3) once the signals $EEG_{sb}(x)$, $EEG_{sb}(y)$ have been fully processed, estimating the occurrence probability $p_X(\pi_i)$ of the motif $\pi_i$ along the signal $EEG_{sb}(x)$, the occurrence probability $p_Y(\pi_i)$ of the motif in along the signal $EEG_{sb}(y)$ and the joint occurrence probability $p_{X,Y}(\pi_i, \pi_j)$ of the two motifs $\pi_i$, $\pi_j$ along said signal $EEG_{sb}(x)$ and said signal $EEG_{sb}(y)$.

In particular, the following is defined:

$$p_X(\pi_i)=\eta_X(\pi_i)/[N-(m-1)L]$$

$$p_Y(\pi_i)=\eta_Y(\pi_i)/[N-(m-1)L] \text{ and}$$

$$p_{X,Y}(\pi_i,\pi_j)=\eta_{X,Y}(\pi_i,\pi_j)/[N-(m-1)L]$$

where L is the time lag between a sample and the next, comprised between 1 and 10. In the embodiment of the method described herein, L=1 is assumed.

As known, the time lag represents the number of samples between a given sample selected from signals $EEG_{sb}(x)$ and $EEG_{sb}(y)$, where each signal $EEG_{sb}(x)$ and $EEG_{sb}(y)$ has N time samples (t, t+1, . . . , t+N−1), and the next sample to be selected. For example, starting from the first sample "t", if m=3 and L=1, the three samples "t", "t+1" and "t+2" will be selected; if, for example, L=5, the samples "t", "t+5", "t+10" will be selected.

For each epoch w the Permutation Jaccard Distance $PJD_{X,Y}(sb)$ between the signal $EEG_{sb}(x)$ and the signal $EEG_{sb}(y)$ is defined by the following relation $$PJD_{X,Y}(sb)=1-PMI(X,Y)/PJE(X,Y),$$

where PMI(X,Y) is the Permutation Mutual Information defined as $$PMI(X,Y)=PE(X)+PE(Y)-PJE(X,Y)$$

where PE(X) is the Permutation Entropy of the signal $EEG_{sb}(x)$ $$PE(X) = -\sum_{i=1}^{m!} p_X(\pi_i) \log(p_X(\pi_i))$$

PE(Y) is the Permutation Entropy of the signal $EEG_{sb}(y)$ $$PE(Y) = -\sum_{i=1}^{m!} p_Y(\pi_i) \log(p_Y(\pi_i))$$

PJE(X,Y) is the Permutation Joint Entropy of the signals $EEG_{sb}(x)$ and $EEG_{sb}(y)$ $$PJE(X, Y) = -\sum_{i=1}^{m!} \sum_{j=1}^{m!} p_{X,Y}(\pi_i, \pi_j) \log(p_{X,Y}(\pi_i, \pi_j))$$

and where log is the natural logarithm.

Preferably but not necessarily, in stage b) it is sufficient to extract, for each epoch w of the first tracing EEG-$T_0$, only two first sub-tracings $EEG_{sb}^{T0}$ corresponding to the two frequency sub-bands delta and theta, and for each epoch w of the second tracing EEG-$T_1$ only two second sub-tracings $EEG_{sb}^{T1}$ corresponding to the two frequency sub-bands delta and theta.

To obtain the input data used in stage a), at time $T_0$ and at time $T_1$, for example with $T_1=(T_0+3 \text{ months})$, electroencephalography (EEG) is used, a technique used to measure and record brain electrical activity. A certain number of electrodes (1, ..., x, y, ..., n) are placed in contact with the patient's scalp. These electrodes are connected to the acquisition system, which amplifies and records the detected electrical potentials. The electrical potentials detected are the result of the overlap of the electrical activity of neuronal populations, where this overlap is of sufficient intensity to be detected by the scalp. Monitoring the spatial-temporal dynamics of the recorded signals allows deducing information about the neural activity that generated them and, consequently, allows obtaining diagnostic information. By way of example, the electrodes are applied to the scalp according to the standard positioning called "10-20 International System". The 10 and 20 refer to 10% and 20% with respect to 100% of the distance between two landmarks called "inion" (protuberance at the base of the occipital bone) and "nasion" (upper attachment of the nose). The electrodes are uniquely identified by a label that identifies the area of belonging (F=frontal, T=temporal, C=central, P=parietal, O=occipital, A=auricular), the hemisphere (even numbers for the right, odd numbers for the left, "z" for the midline) and the exact position. There are different types of electrode positioning, called "montages", which are set up to provide a uniform view of the distribution of the cortical electrical activity. In a certain time instant t, the value detected by the single electrode V represents the potential difference with respect to a reference electrode V(t)-Vref(t). In the proposed example, the EEG is recorded according to the 10-20 International System (montage: Fp1, Fp2, F3, F4, C3, C4, P3, P4, O1, O2, F7, F8, T3, T4, T5, T6, Fz, Cz e Pz), with linked ear-lobe reference (A1-A2). For example, the recording time is 3-7 minutes, preferably 5 minutes. Preferably, during the acquisition the patients sit comfortably, keep their eyes closed but remain awake (eye closed resting state).

EEG signals are filtered in the 0.5-30 Hz range, to include four sub-bands of interest, delta (0.5-4 Hz), theta (4-8 Hz), alpha (8-13 Hz), beta (13-30 Hz), and sampled with a predetermined sampling frequency, for example fs=256 Hz.

Preferably, the EEG tracing is then viewed by the EEG expert in order to find and exclude any sleep patterns and to label and eliminate segments that exhibit artifacts. If the sampling frequency is higher than 256 Hz, a 256 Hz downsampling will be performed.

The EEG tracing thus acquired is divided into epochs w of equal duration and not overlapping, of about 3-7 seconds, for example 5 seconds, and is then divided into four sub-tracings $EEG_{sb}$ (stage b), each associated with one of the specific sub-bands of interest: $EEG_{delta}$, $EEG_{theta}$, $EEG_{alfa}$, $EEG_{beta}$.

The sub-tracings are extracted by filtering, in a known manner, each EEG channel through bandpass filters based on the Fast Fourier Transform (FFT) and on the reverse FFT (IFFT). By means of the FFT, each EEG signal is broken down into its different elementary frequency components; by means of the IFFT, the EEG signal is then reconstructed in the desired specific sub-band, that is: delta (0.5-4 Hz), theta (4-8 Hz), alpha (8-13 Hz) and beta (13-30 Hz).

Each of the sub-tracings $EEG_{sb}$ thus obtained ($EEG_{delta}$, $EEG_{theta}$, $EEG_{alpha}$, $EEG_{beta}$), divided into epochs w, is then analyzed independently from the others.

The concepts underlying the invention are described below, including that of considering the scalp as a network where the electrodes represent the nodes. An appropriate measure of dissimilarity is defined between each pair of electrodes x, y (with x=1, ..., n; y=1, ..., n and x≠y), which can represent the coupling strength between the areas covered by the two electrodes x and y. The "inter-electrode" dissimilarity is quantified by estimating the coupling strength between the corresponding signals $EEG_{sb}(x)$ and $EEG_{sb}(y)$. In this way it is possible to associate a graph to the EEG recorded at time $T_0$ and a graph to the EEG recorded at time $T_1$.

These dissimilarities between electrodes are then passed through a hierarchical clustering (HC), so as to group the electrodes according to the coupling strength between corresponding EEG signals. The clusters depend on the selected threshold of fusion level FL.

Given a threshold of fusion level FL, a set of clusters is determined and it is possible to subsequently estimate the network density or connectivity density. By comparing the connectivity density of the two graphs, corresponding to time $T_0$ and time $T_1$, it is possible to indirectly quantify how the brain connectivity varies.

Other concepts underlying the invention are explained in more detail hereinafter. Permutation Entropy (PE) was introduced by Bandt and Pompe (C. Bandt and B. Pompe—Permutation entropy: A natural complexity measure for time series—Phys. Rev. Lett., 88 (17), 2002) as a symbolic descriptor of dynamic complexity changes in time series. Thanks to the projection in symbols (motifs), the Permutation Entropy, or simply PE, estimates the randomness of a time series regardless of its amplitude, which plays a key role when analyzing the EEG. In fact, the amplitude of EEG, recorded through a given electrode, depends on the distance from the reference electrode. When processing EEG recordings using amplitude-dependent techniques, each EEG signal should first be normalized to cancel the effect of closeness to the reference electrode. Normalization is not necessary when a symbolic procedure such as PE is used. However, PE is a univariate descriptor that can only describe the randomness of a single time series, in this case an EEG signal, and cannot quantify the coupling strength between two or more time series, i.e. between two or more EEG signals.

Advantageously, the descriptor proposed in the method of the invention, namely the Permutation Jaccard Distance (PJD), is based on the same projection into symbols adopted by Permutation Entropy (PE), but is a multivariate descriptor that can quantify the coupling strength between two or more time series.

From the Information Theory, given a time series x, with N samples, and its probability density function p(x), the Entropy of the series x is defined as $$H(X) = -\sum_{i=1}^{N} p_X(x_i) \log(p_X(x_i))$$

Given two time series x and y, with N samples, and their joint probability density function $p_{X,Y}(x, y)$, their Joint Entropy is defined as:

$$H(X, Y) = -\sum_{i=1}^{N}\sum_{j=1}^{N} p_{X,Y}(x_i, y_j) \log(p_{X,Y}(x_i, y_j))$$

Their Mutual Information is defined as $MI(X;Y)=H(X)+H(Y)-H(X,Y)$.

The Variation of Information is defined as $VI(X,Y)=H(X,Y)-MI(X;Y)$.

When normalized, $VI(X,Y)$ becomes the Jaccard Distance between the time series x and y $$JD(X,Y)=1-MI(X;Y)/H(X,Y)$$

which is a metric because it satisfies the properties of symmetry, positivity, boundedness ($0 \leq JD(X, Y) \leq 1$) and triangular inequality (A. Kraskov, H. Stogbauer, R. G. Andrzejak, and P. Grassberger—Hierarchical clustering based on mutual information—arXiv:q-bio/0311039).

The concept of Permutation Jaccard Distance (PJD) is then introduced by exploiting the properties of JD as well as the advantages of projecting time series into symbols (motifs), which are particularly useful when analyzing EEG signals.

As for the time series projection in symbols, given two time series x and y with N samples, they can be mapped into an m-dimensional space, where m is the embedding dimension [N. Packard, J. Crutchfield, J. Farmer and R. Shaw, "Geometry from time series", Phys. Rev. Lett. 45, (1980) 712.]

Given an EEG epoch under analysis, starting from two given samples x(t) and y(t) and given a time lag L, two m-dimensional vectors, $X_t$ and $Y_t$ can be constructed as follows:

$$X_t=[x(t), \ldots, x(t+L), x(t+(m-1)L)]^T$$

and $$Y_t=[y(t), y(t+L), \ldots, y(t+(m-1)L)]T,$$

where the apex T indicates the transposed.

Figure 1:
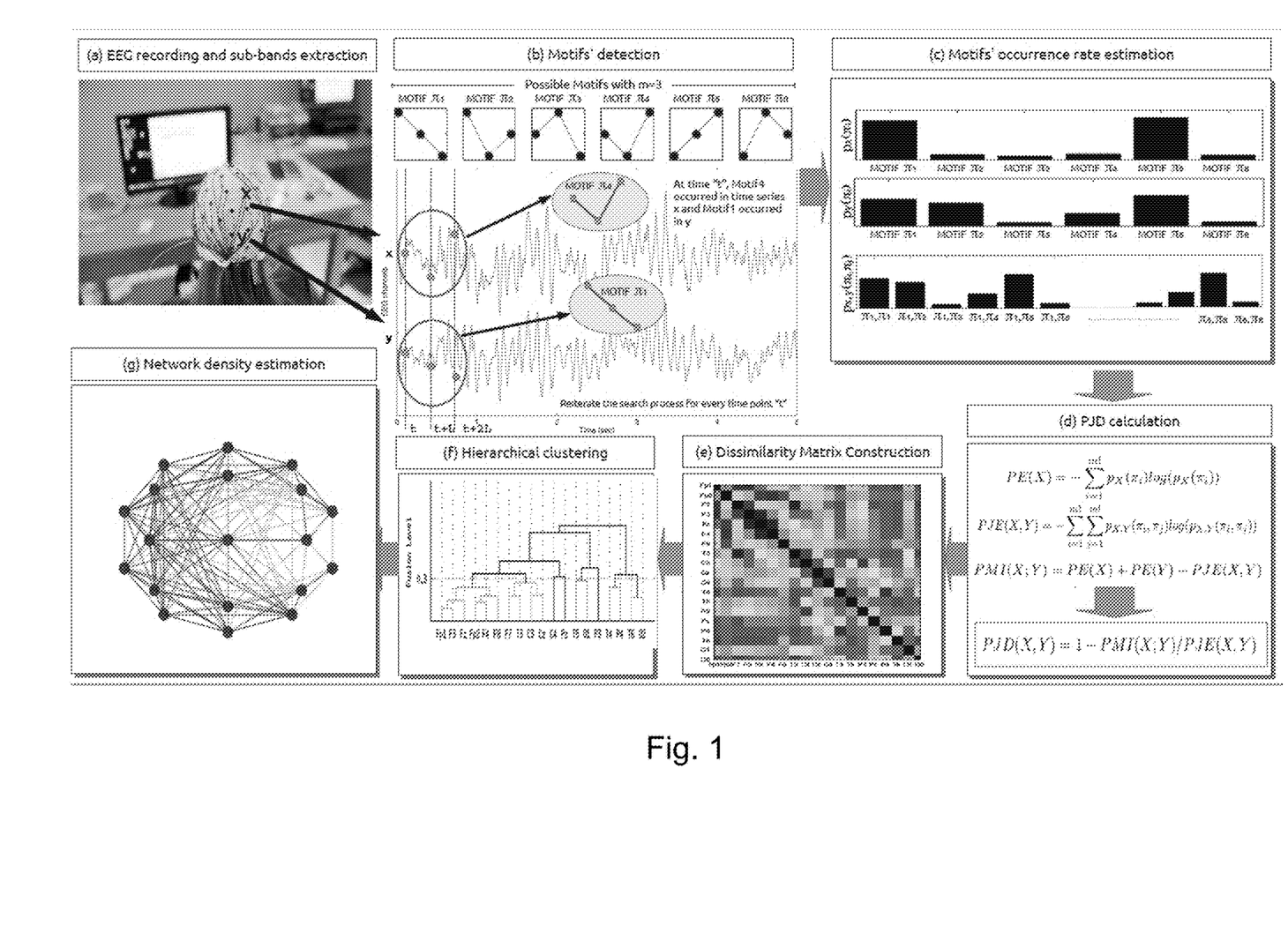
FIG. 1 shows a diagram of an embodiment of the method of the invention.

The methodology is illustrated schematically using as an example m=3 and L=1 (FIG. 1). $X_t$ and $Y_t$ are both vectors with three elements. The algorithm eliminates the absolute values of $X_t$ and $Y_t$ and takes into account only the relative amplitude of their elements: low, medium, high. If we consider three possible levels (m=3), six possible (m!=6) ordinal sequences (patterns or motifs) can be identified, that is, the permutations without repetition of the three levels low, medium and high. Motifs or patterns are indicated with $\pi_i$, where i=1, ..., 6 (FIG. 1). The algorithm checks which motif occurs in $X_t$ (motif $\pi_4$ in the example shown in FIG. 1) and which motif occurs in $Y_t$ (motif $\pi_1$ in the example of FIG. 1). According to the example in FIG. 1, in the first iteration, the algorithm will increment the number of occurrences $\eta_X(\pi_4)$ of the motif $\pi_4$ in the time series x, and the number of occurrences $\eta_Y(\pi_i)$ of the motif $\pi_1$ in the time series y. The algorithm will also increment the number of joint occurrences $\eta_{X,Y}(\pi_4, \pi_1)$ of the two motifs $\pi_4$ and $\pi_1$. Then the algorithm moves to the following samples x(t+1), y(t+1), constructs two new vectors $X_{t+1}$ and $Y_{t+1}$ and reiterates the procedure just illustrated.

Once the iterations have been completed and the two time series have been fully processed, the algorithm estimates the overall probability that a given motif $\pi_i$ occurs (with i=1, ..., 6) in the time series x and in the time series y, normalizing the number of occurrences $\eta$ by the number of iterations:

$$p_X(\pi_i)=\eta_X(\pi_i)/[N-(m-1)L]$$

$$p_Y(\pi_i)=\eta_Y(\pi_i)/[N-(m-1)L]$$

as well as the probability that a couple of motifs occurs jointly:

$$p_{X,Y}(\pi_i,\pi_j)=\eta_{X,Y}(\pi_i,\pi_j)/[N-(m-1)L].$$

Advantageously, by discarding the absolute amplitude of the elements of the vectors $X_t$ and $Y_t$ and matching them with the predetermined patterns, the procedure becomes amplitude independent. This feature is very useful when analyzing EEG signals, because a signal recorded through an electrode close to the reference electrode will inherently have a lower amplitude, compared to a electrode located farther away.

Therefore, given a time series x, with N samples and embedding dimension m, the Permutation Entropy of the series x is defined as $$PE(X) = -\sum_{i=1}^{m!} p_X(\pi_i) \log(p_X(\pi_i))$$

Given two time series x and y, with N samples and embedding dimension m, their Permutation Joint Entropy (PJE) is defined as $$PJE(X, Y) = -\sum_{i=1}^{m!}\sum_{j=1}^{m!} p_{X,Y}(\pi_i, \pi_j) \log(p_{X,Y}(\pi_i, \pi_j))$$

Their Permutation Mutual Information is defined as $$PMI(X,Y)=PE(X)+PE(Y)-PJE(X,Y).$$

Their Permutation Variation of Information (PVI) is defined as $$PVI(X,Y)=PJE(X,Y)-PMI(X,Y).$$

Therefore the Permutation Jaccard Distance PJD between time series x and y is defined as $$PJD(X,Y)=1-PMI(X,Y)/PJE(X,Y).$$

When the coupling strength between the series x and the series y increases, a decrease in PJD is expected, because the two time series become more synchronized. In fact, as the coupling strength increases, PMI increases and joint randomness (therefore PJE) decreases.

As a consequence of the definition of Jaccard Distance (JD), the PJD satisfies the properties of a metric and is bounded between 0 and 1.

The advantages of using PJD are numerous, since PJD is a symbolic methodology, it is less sensitive to artifacts because it projects the EEG time series into a set of symbols (motifs). In this way, the possible amplitude variation in the EEG signal, due to artifacts, would not alter the amplitude of the symbols, which are predetermined. Furthermore, PJD is nonlinear and could capture nonlinear dynamics in the EEG signal better than linear descriptors of the coupling strength, such as coherence (Wavelet Coherence).

The Permutation Jaccard Distance between each possible pair of signals (electrodes) is calculated, for each patient, in each frequency sub-band, for both EEG-$T_0$ and EEG-$T_1$ tracings. Given a sub-band sb (delta, theta, alpha or beta) and the corresponding sub-tracing $EEG_{sb}$, and given a generic epoch w under analysis, the Permutation Jaccard Distance is calculated between each pair of signals $EEG_{sb}(x)$ and $EEG_{sb}(y)$, i.e. between each pair of electrodes x and y (with x=1, . . . , n; y=1, . . . , n and x≠y), both for the measurement recorded at time $T_0$ and for the measurement recorded at time $T_1$ (stage c).

These values $PJD_{X,Y^w}(sb)$ are therefore averaged over time, i.e. over all the epochs w, to obtain the respective average values $PJD^{T0}_{X,Y}(sb)$, $PJD^{T1}_{X,Y}(sb)$ for each possible pair of signals $EEG_{sb}(x)$ and $EEG_{sb}(y)$ in each sub-band sb.

In the method of the invention, a hierarchical Clustering HC is used to group the signals, and therefore the electrodes, according to their mutual Permutation Jaccard Distances (PJDs) and subsequently to estimate the connectivity density of the electrode network.

Hierarchical clustering partitions a sample dataset into clusters. There are two types of hierarchical clustering: agglomerative and divisive. The divisive hierarchical clustering assigns the entire dataset to a cluster and then iteratively splits it into groups until all groups are single clusters. However, this algorithm is computationally expensive. In the method of the invention, it is preferable to use an agglomerative hierarchical clustering which assigns an individual cluster to each data point and then, in an iterative manner, merges the two most similar clusters. The procedure is repeated until all subsets belong to a single cluster (Brian S. Everitt, Sabine Landau, Morven Leese, Daniel Stahl. Cluster Analysis, 5th Edition (2011). Wiley. ISBN: 978-0-470-74991-3).

Several agglomerative HC algorithms have been proposed in the literature (Brian S. Everitt, Sabine Landau, Morven Leese, Daniel Stahl. Cluster Analysis, 5th Edition (2011). Wiley. ISBN: 978-0-470-74991-3). Preferably, in the method of the invention a "complete linkage algorithm" is used, also called "furthest neighbour", which defines the distance or dissimilarity between two clusters by means of the maximum distance between a pair of signals.

Said mean values $PJD^{T0}_{X,Y}(sb)$ and $PJD^{T1}_{X,Y}(sb)$ thus define the dissimilarity $D_{X,Y}^{T0}(sb)$ and $D_{X,Y}^{T1}(sb)$ between the signal $EEG_{sb}(x)$ and the signal $EEG_{sb}(y)$ of each possible pair of signals, respectively at the time $T_0$ and at the time $T_1$, i.e. between two electrodes of each possible pair of electrodes.

In this way, two dissimilarity matrices $D^{T0}(sb)$ and $D^{T1}(sb)$ are created in each frequency sub-band, the (x,y)-th element of which is equal to $D_{X,Y}^{T0}(sb)=PJD_{X,Y}^{T0}(sb)$ and $D_{X,Y}^{T1}(sb)=PJD_{X,Y}^{T1}(sb)$, respectively. Substantially, two networks $NET_{sb}(T_i)$ are constructed, with i=0, 1, the node "x" of which represents the signal $EEG_{sb}(x)$ at the time $T_i$, and the weight that connects the nodes "x" and "y" of the network $NET_{sb}(T_i)$ represents the dissimilarity between the pair of signals $EEG_{sb}(x)$ and $EEG_{sb}(y)$ at time $T_i$. In this way, it is possible to create a dissimilarity matrix $D^{T1}(sb)$ for each phase of the follow-up $T_i$ of each patient and for each sub-band.

At this point, the hierarchical Clustering HC is applied to the dissimilarity matrices $D^{T0}(sb)$ and $D^{T1}(sb)$, having as output for each frequency sub-band two dendrograms showing the connection among the first signals $EEG_{sb}(1, \ldots n)$ at time $T_0$ and the connection among the second signals $EEG_{sb}(1, \ldots n)$ at time $T_1$, respectively, as a function of a fusion level FL, i.e. two dendrograms showing respectively the connections of the first set of signals $EEG_{sb}(1, \ldots n)$ at the time $T_0$ and the connections of the second set of signals $EEG_{sb}(1, \ldots n)$ at time $T_1$ as a function of a fusion level FL.

The dendrogram therefore provides a view of the connection between the electrodes as a function of the fusion level (stage d). Given a fusion level FL, the electrodes connected at a level below FL will belong to the same cluster and will be considered connected. Therefore, for each dissimilarity matrix and each fusion level FL, a set of clusters is determined (see for example FIG. 2 or 3).

Thereafter (stage e), the number of active connections $AC_{FL}^{T0}(sb)$ and $AC_{FL}^{T1}(sb)$ is calculated for each fusion level FL, respectively by summing the number of possible pairs of first signals $EEG_{sb}(1, \ldots n)$ at time $T_0$, and summing the number of possible pairs of second signals $EEG_{sb}(1, \ldots n)$ at time $T_1$, present within each cluster of the respective set of clusters. That is, the number of active connections $AC_{FL}^{T0}(sb)$ and $AC_{FL}^{T1}(sb)$ is calculated for each fusion level FL, by summing the number of signal pairs belonging to the first set of signals $EEG_{sb}(1, \ldots n)$ at time $T_0$, which are connected for that given fusion level FL (that is to say, they are part of the same cluster in the dendrogram), and by summing the number of signal pairs belonging to the second set of signals $EEG_{sb}(1, \ldots n)$ at time $T_1$, which are connected for that given fusion level, respectively.

Noting that the total number of possible connections between n nodes of a network is equal to $[n*(n-1)/2]$, the network densities $ND_{FL}^{T0}(sb)$ and $ND_{FL}^{T1}(sb)$ are defined for each fusion level FL by normalizing the number of active connections $AC_{FL}^{T0}(sb)$ and $AC_{FL}^{T1}(sb)$ with respect to the total number of possible connections, where n is the number of signals (electrodes).

In general, we have $$ND_{FL}^{T_i}(sb) = \frac{AC_{FL}^{T_i}(sb)}{n*(n-1)/2}.$$

Therefore, ND represents the ratio between the number of active connections and the number of potential connections of a network, whereby ND=0 represents a totally disconnected network while ND=1 represents a completely interconnected network.

Figure 2:
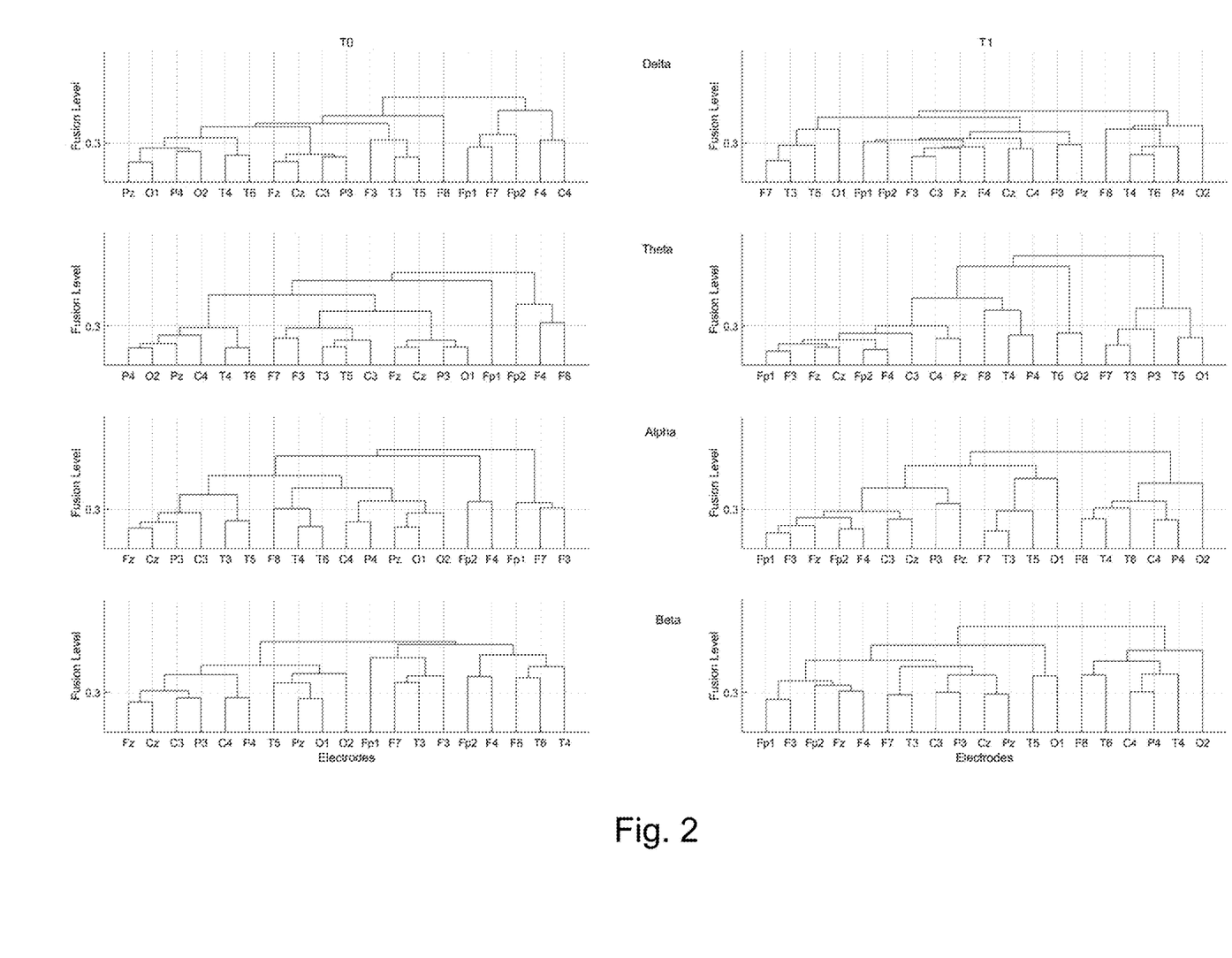
FIG. 2 shows a series of dendrograms, relating to a first patient, for each sub-band (sb) at time $T_0$ and at time $T_1$.
Figure 3:
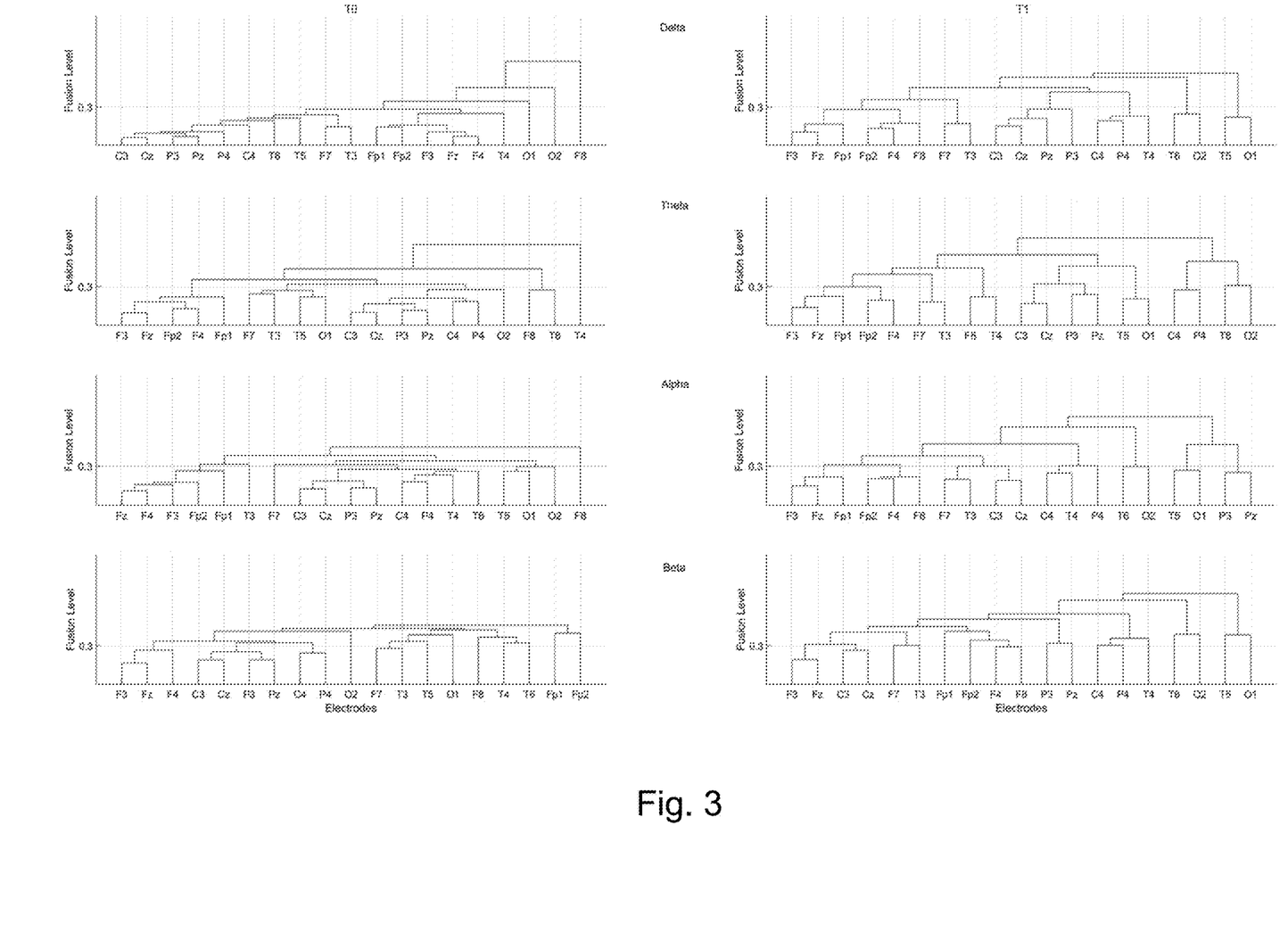
FIG. 3 shows a series of dendrograms, relating to a second patient, for each sub-band (sb) at time $T_0$ and at time $T_1$.

The dendrograms of two patients are illustrated by way of example in FIGS. 2 and 3. The dendrogram in FIG. 2 refers to a first patient Pt30 with stable MCI at time while the dendrogram in FIG. 3 refers to a patient Pt51 in which there was the conversion from MCI to Alzheimer's disease (AD) at time $T_1$.

The axis of the ordinates of the dendrogram represents the distance or dissimilarity between the clusters (fusion level FL). The axis of the abscissas of the dendrogram represents the electrodes. Each branch of the diagram (vertical line) corresponds to a cluster. The (horizontal) conjunction line of two or more branches identifies the distance (fusion level) at which the clusters merge.

In order to provide a view at-a-glance of how connectivity changed from $T_0$ to $T_1$, an arbitrary fusion level was selected (0,3), both for $T_0$ and for $T_1$, and the corresponding clusters are highlighted in FIGS. 2 and 3 with different colors. It is worth noting that while the clusters have barely changed for the patient Pt30 (stable), they have instead changed significantly for the patient Pt51 (converted). For example, in the delta band, at the time $T_0$, 3 single elements were observed and a large cluster with 16 elements was obtained, while, at the time $T_1$, 6 clusters were obtained, with a size ranging from 2 to 6 elements.

In order to quantify such a visual evaluation, the network densities $ND_{FL}^{T0}(sb)$ and $ND_{FL}^{T1}(sb)$ were estimated as described above. ND indicates how many connections are active as a function of the threshold of the selected fusion level. The network densities $ND_{FL}^{T0}(sb)$ and $ND_{FL}^{T1}(sb)$ were calculated for different fusion level thresholds ranging from 0 to 1, with a step of 0.01. The fusion level is between 0 and 1 because the PJD is by definition included in that range.

Figure 4:
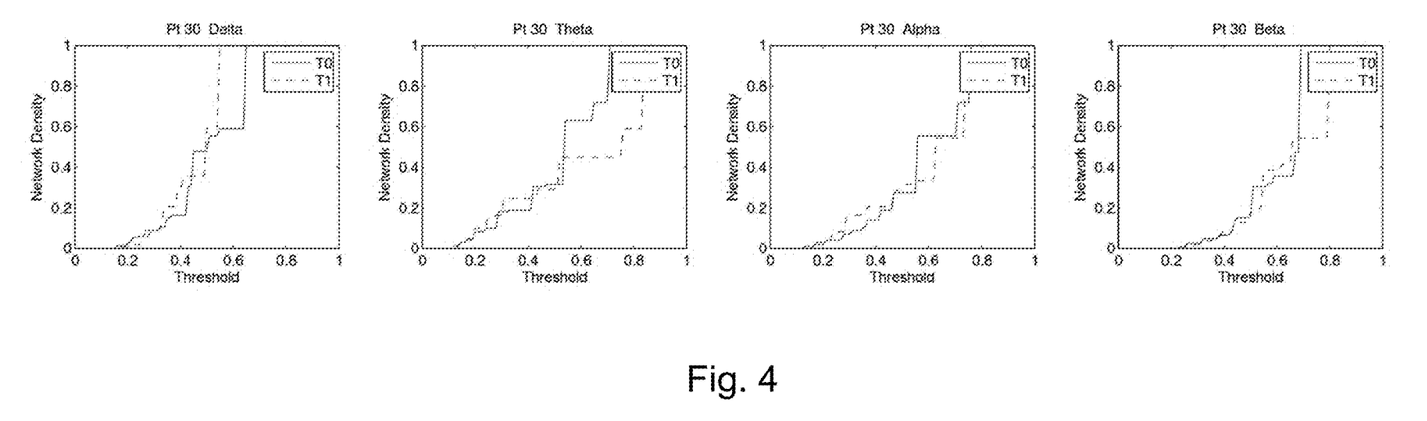
FIG. 4 shows the trend of the network density, relative to the first patient, as a function of the fusion level, for each sub-band (sb) at time $T_0$ and at time $T_1$.
Figure 5:
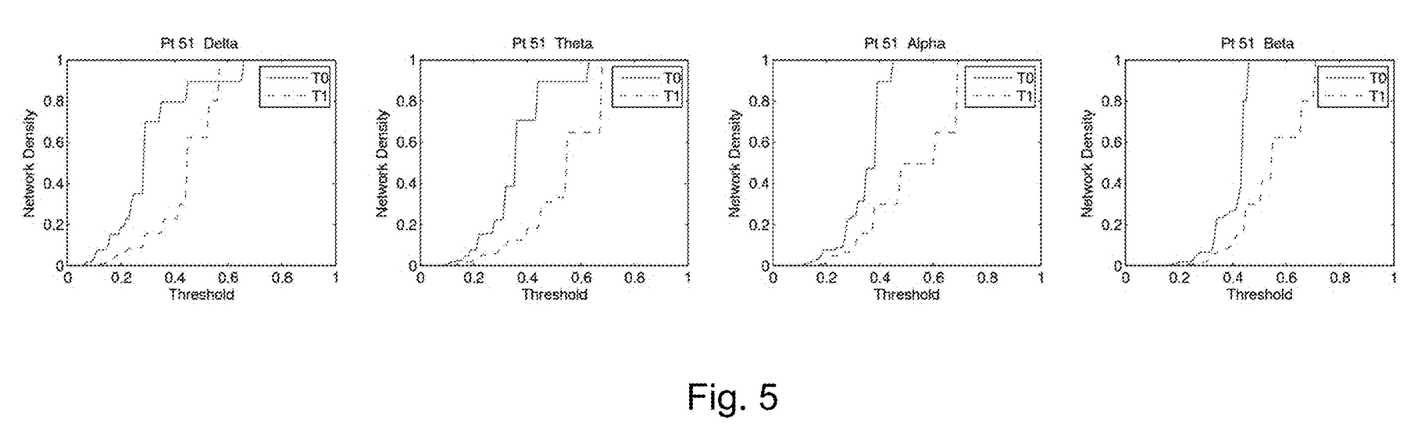
FIG. 5 shows the trend of the network density, relative to the second patient, as a function of the fusion level, for each sub-band (sb) at time $T_0$ and at time $T_1$.

FIGS. 4 and 5 show explanatory representations of the evolution of the network density from $T_0$ to $T_1$ as a function of the fusion level threshold, in each sub-band, for the patient Pt30 (stable MCI) and for the patient Pt51 (converted AD), respectively.

Regarding the patient Pt30 (FIG. 4), it is observed that the two patterns $ND^{T0}$ and $ND^{T1}$ essentially overlap for FL<0.55 in each sub-band, while they differ significantly for the patient Pt51 also for FL<0.55. This result indicates that the network density changes significantly in the patient Pt51 in the transition from $T_0$ to $T_1$ while remaining stable in the patient Pt30.

In order to quantify the results shown in FIGS. 4 and 5, the percentage variation $\Delta ND(sb)$ % of the area below the two curves $ND^{T1}(sb)$ and $ND^{T0}(sb)$ for each frequency sub-band is calculated with the formula $$\Delta ND(sb)\% = (ND^{T1}(sb) - ND^{T0}(sb)) * 100 / ND^{T0}(sb).$$

It has been found experimentally that the patients converted into AD have undergone a negative percentage variation $\Delta ND(sb)$ % for each frequency sub-band in the transition from $T_0$ to $T_1$. No false positive was found.

Advantageously, the method of the present invention for the indirect estimation of the density of brain connectivity is extremely sensitive and specific for the conversion from MCI to AD. The use of the PJD as a symbolic descriptor of the coupling strength gave better results than the linear descriptors of the coupling strength, such as coherence (Wavelet Coherence), which instead led to the detection of false positives.

The invention claimed is:

1. A method for detecting a conversion from mild cognitive impairment (MCI) to Alzheimer disease (AD), the method comprising the following stages:
   a) providing as input data a plurality of first signals EEG (1, ..., n) recorded at a first time $T_0$ and defining a first tracing EEG-$T_0$ of a patient with mild cognitive impairment, and a plurality of second signals EEG (1, ..., n) recorded at a second time $T_1$ and defining a second tracing EEG-$T_1$ of the same patient, each first signal and each second signal corresponding to a respective electrode V (with V=1, ..., n), and the first tracing EEG-$T_0$ and the second tracing EEG-$T_1$ being divided into epochs (w) of equal duration;
   b) for each epoch (w) of the first tracing EEG-$T_0$ extracting at least two first sub-tracings $EEG_{sb}^{T0}$ corresponding to a respective frequency sub-band (sb=delta, theta), and for each epoch (w) of the second tracing EEG-$T_1$ extracting at least two second sub-tracings $EEG_{sb}^{T1}$ corresponding to a respective frequency sub-band (sb=delta, theta);
   c) for each epoch (w) and for each of the first sub-tracings $EEG_{sb}^{T0}$ and second sub-tracings $EEG_{sb}^{T1}$, for each possible pair of signals x and y (with x=1, ..., n; y=1, ..., n and x≠y) calculating a Permutation Jaccard Distance $PJD_{X,Y^w}(sb)$ between signal $EEG_{sb}(x)$ and signal $EEG_{sb}(y)$ at both time $T_0$ and time $T_1$;
   d) for each first sub-tracing $EEG_{sb}^{T0}$ and each second sub-tracing $EEG_{sb}^{T1}$, performing a hierarchical Clustering to divide into clusters the signals of the respective sub-tracing according to their mutual Permutation Jaccard Distances;
   e) estimating a network density, when a fusion level FL varies, from the clusters obtained by the hierarchical Clustering, defining two curves $ND^{T0}(sb)$ and $ND^{T1}(sb)$ for each frequency sub-band (sb=delta, theta);
   f) calculating a percentage variation $\Delta ND(sb)$ % of an area subtended by the two curves $ND^{T1}(sb)$ and $ND^{T0}(sb)$ for each frequency sub-band with the formula $\Delta ND(sb)\% = (ND^{T1}(sb) - ND^{T0}(sb)) * 100 / ND^{T0}(sb)$;
   g) verifying that said percentage variation $\Delta ND(sb)$ % is negative for each frequency sub-band in a transition from $T_0$ to $T_1$ to confirm the conversion from mild cognitive impairment (MCI) to Alzheimer disease (AD).

2. The method according to claim 1, wherein between stage c) and stage d) for each first sub-tracing $EEG_{sb}^{T0}$ and each second sub-tracing $EEG_{sb}^{T1}$ the following is provided:
   calculating respective average values $PJD^{T0}_{X,Y}(sb)$, $PJD^{T1}_{X,Y}(sb)$ on all the epochs (w) for each possible pair of signals $EEG_{sb}(x)$ and $EEG_{sb}(y)$, said average values $PJD^{T0}_{X,Y}(sb)$ and $PJD^{T1}_{X,Y}(sb)$ defining dissimilarities $D_{X,Y}^{T0}(sb)$ and $D_{X,Y}^{T1}(sb)$ between said signal $EEG_{sb}(x)$ and said signal $EEG_{sb}(y)$ of each possible pair, at time $T_0$ and at time $T_1$, respectively;
   building two networks $NET_{sb}(T_i)$, with i=0, 1, a node "x" of which represents signal $EEG_{sb}(x)$ at time and a weight connecting the nodes "x" and "y" of the network $NET_{sb}(T_i)$ represents the dissimilarity between the pair of signals $EEG_{sb}(x)$ and $EEG_{sb}(y)$ at time thus creating two dissimilarity matrices $D^{T0}(sb)$ and $D^{T1}(sb)$, the (x, y)-th element of which is equal to $D_{X,Y}^{T0}(sb) = PJD_{X,Y}^{T0}(sb)$ and $D_{X,Y}^{T1}(sb) = PJD_{X,Y}^{T1}(sb)$, respectively.

3. The method according to claim 2, wherein in stage d) the hierarchical Clustering is performed, from the dissimilarity matrices $D^{T0}(sb)$ and $D^{T1}(sb)$, outputting two dendrograms showing a connection between the first signals $EEG_{sb}(1, ..., n)$ at time $T_0$ and a connection between the second signals $EEG_{sb}(1, ..., n)$ at time $T_1$, respectively, as a function of the fusion level FL, whereby for each dissimilarity matrix and for each fusion level FL, the set of clusters is determined.

4. The method according to claim 3, wherein in stage e), the following is provided
   for each fusion level FL, calculating the number of active connections $AC_{FL}^{T0}(sb)$ and $AC_{FL}^{T1}(sb)$ by summing the number of possible pairs of first signals $EEG_{sb}(1, ..., n)$ at time $T_0$, which result to be connected for a predetermined fusion level FL, and summing the number of possible pairs of second signals $EEG_{sb}(1, ..., n)$ at time $T_1$, which result to be connected for said predetermined fusion level, respectively;
   for each fusion level FL, estimating the network densities $ND_{FL}^{T0}(sb)$ and $ND_{FL}^{T1}(sb)$ by normalizing $AC_{FL}^{T0}(sb)$ and $AC_{FL}^{T1}(sb)$ with respect to the total number of possible connections equal to $[n*(n-1)/2]$, where n is the number of signals.

5. The method according to claim 4, wherein the network densities $ND_{FL}^{T0}(sb)$ and $ND_{FL}^{T1}(sb)$ are estimated for different fusion levels from 0 to 1, preferably with steps of 0.01.

6. The method according to claim 1, wherein in stage c), before calculating the Permutation Jaccard Distance $PJD_{X,Y}(sb)$ for each possible pair of signals $EEG_{sb}(x)$ and $EEG_{sb}(y)$, the following is provided:

c1) for each possible pair of signals $EEG_{sb}(x)$ and $EEG_{sb}(y)$ which is mappable in a m-dimensional space, each signal $EEG_{sb}(x)$, $EEG_{sb}(y)$ having N time samples (t, t+1, ... t+N−1) in said epoch (w), detecting a plurality of symbols $\pi_i$, $\pi_j$, with i, j=1, ..., m!, occurring in said epoch (w) for each sample (t, t+1, ..., t+N−1);

c2) for each sample (t, t+1, ..., t+N−1), detecting the number of occurrences $\eta_X(\pi_i)$ of each symbol m along the signal $EEG_{sb}(x)$, the number of occurrences $\eta_Y(\pi_i)$ of each symbol m along the signal $EEG_{sb}(y)$, and the number of joint occurrences $\eta_{X,Y}(\pi_i,\pi_j)$ of the two symbols $\pi_i$, $\pi_j$ along said signal $EEG_{sb}(x)$ and said signal $EEG_{sb}(y)$;

c3) once the signals $EEG_{sb}(x)$, $EEG_{sb}(y)$ have been fully processed, estimating the occurrence probability $p_X(\pi_i)$ of the symbol m along the signal $EEG_{sb}(x)$, the occurrence probability $p_Y(\pi_i)$ of the symbol m along the signal $EEG_{sb}(y)$ and the joint occurrence probability $p_{X,Y}(\pi_i, \pi_j)$ of the two symbols $\pi_i$, $\pi_j$ along said signal $EEG_{sb}(x)$ and said signal $EEG_{sb}(y)$.

7. The method according to claim 6, wherein $p_X(m) = \eta_X(\pi_i)/[N-(m-1)L]$ $p_Y(\pi_i) = \eta_Y(\pi_i)/[N-(m-1)L]$ and $p_{X,Y}(\pi_i,\pi_j) = \eta_{X,Y}(\pi_i,\pi_j)/[N-(m-1)L,]$ where L is a time lag between a sample and the next.

8. The method according to claim 7, wherein for each epoch (w) the Permutation Jaccard Distance $PJD_{X,Y}(sb)$ between said signal $EEG_{sb}(x)$ and said signal $EEG_{sb}(y)$ is defined by the following relation $PJD_{X,Y}(sb) = 1 - PMI(X,Y)/PJE(X,Y)$, where PMI(X,Y) is the Permutation Mutual Information defined as $PMI(X,Y) = PE(X) + PE(Y) - PJE(X,Y)$ where PE(X) is the Permutation Entropy of signal $EEG_{sb}(x)$ $$PE(X) = -\sum_{i=1}^{m!} p_X(\pi_i) \log(p_X(\pi_i))$$

PE(Y) is the Permutation Entropy of signal $EEG_{sb}(y)$ $$PE(Y) = -\sum_{i=1}^{m!} p_Y(\pi_i) \log(p_Y(\pi_i))$$

and PJE(X,Y) is the Permutation Joint Entropy of signals $EEG_{sb}(x)$ and $EEG_{sb}(y)$ $$PJE(X,Y) = -\sum_{i=1}^{m!} \sum_{j=1}^{m!} p_{X,Y}(\pi_i, \pi_j) \log(p_{X,Y}(\pi_i, \pi_j))$$

where log is a natural logarithm.

9. The method according to claim 1, wherein the hierarchical Clustering is performed by an agglomerative hierarchical Clustering algorithm, preferably a "complete linkage algorithm", also referred to as "furthest neighbour".

10. The method according to claim 1, wherein in stage b) for each epoch (w) of the first tracing $EEG-T_0$ four first sub-tracings $EEG_{sb}^{T0}$ are extracted, corresponding to a respective frequency sub-band (sb=delta, theta, alpha, beta), and for each epoch (w) of the second tracing $EEG-T_1$, four second sub-tracings $EEG_{sb}^{T1}$ are extracted, corresponding to a respective frequency sub-band (sb=delta, theta, alpha, beta).

11. The method according to claim 1, wherein for each epoch (w) the Permutation Jaccard Distance $PJD_{X,Y}(sb)$ between said signal $EEG_{sb}(x)$ and said signal $EEG_{sb}(y)$ is defined by the following relation $PJD_{X,Y}(sb) = 1 - PMI(X,Y)/PJE(X,Y)$, where PMI(X,Y) is the Permutation Mutual Information defined as $PMI(X,Y) = PE(X) + PE(Y) - PJE(X,Y)$ where PE(X) is the Permutation Entropy of signal $EEG_{sb}(x)$ $$PE(X) = -\sum_{i=1}^{m!} p_X(\pi_i) \log(p_X(\pi_i))$$

PE(Y) is the Permutation Entropy of signal $EEG_{sb}(y)$ $$PE(Y) = -\sum_{i=1}^{m!} p_Y(\pi_i) \log(p_Y(\pi_i))$$

and PJE(X,Y) is the Permutation Joint Entropy of signals $EEG_{sb}(x)$ and $EEG_{sb}(y)$ $$PJE(X,Y) = -\sum_{i=1}^{m!} \sum_{j=1}^{m!} p_{X,Y}(\pi_i, \pi_j) \log(p_{X,Y}(\pi_i, \pi_j))$$

where log is a natural logarithm.

* * * * *